United States Patent [19]
Ellman et al.

[11] Patent Number: 5,395,368
[45] Date of Patent: Mar. 7, 1995

[54] MULTIPLE-WIRE ELECTROSURGICAL ELECTRODES

[76] Inventors: Alan G. Ellman; Jon C. Garito, both of 1135 Railroad Ave., Hewlett, N.Y. 11557

[21] Appl. No.: 63,727

[22] Filed: May 20, 1993

[51] Int. Cl.⁶ .............................................. A61B 17/39
[52] U.S. Cl. ...................................................... 606/45
[58] Field of Search ........................... 606/44, 45, 48.5

[56] References Cited

U.S. PATENT DOCUMENTS

| | | | |
|---|---|---|---|
| 2,249,894 | 7/1941 | Goldenstein | 606/50 |
| 4,033,351 | 7/1977 | Hetzel | 606/48 |

FOREIGN PATENT DOCUMENTS 275642  7/1988  European Pat. Off. .............. 606/49

*Primary Examiner*—Lee S. Cohen

[57] ABSTRACT

A multiple-wire electrode for use with an electrosurgical handpiece in an electrosurgical medical, dental, or veterinarian procedure, which comprises an electrically-conductive shaft having one end sized to fit on an electrosurgical handpiece and plural spaced electrically-conductive wires electrically connected to the opposite end of the shaft. The ends of the wires are electrically active, whereby when the wire ends are applied to tissue of a patient and the handpiece energized, electrical currents will flow simultaneously from the wire ends to the tissue allowing simultaneous cutting by electrical currents of parallel incisions when the handpiece is drawn across the tissue. Means can be provided connected to the shaft for varying the spacing between the wire ends. The electrode of the invention is of particular use in connection with the harvesting of hair follicles in a hair transplant procedure.

12 Claims, 3 Drawing Sheets

MULTIPLE-WIRE ELECTROSURGICAL ELECTRODES

This invention relates to electrosurgical electrodes for medical, dental, or veterinarian procedures.

BACKGROUND OF THE INVENTION

A known procedure for hair transplants, called graft harvesting, involves surgically removing strips of scalp containing many hair follicles. The strip is then cut into smaller pieces each containing one or more hair follicles and used as grafts in scalp areas devoid of hair. The known procedure uses a double- or trip-bladed knife as a scalpel with which the surgeon makes simultaneously two, respectively three, parallel shallow incisions which must be parallel with the hair shafts and should avoid, i.e., cuts around, usable hair shafts. Ideally, the incisions should be to the same depth. These constraints require that the blades remain parallel with the hair throughout the cutting procedure, and that the cutting pressure applied to the scalpel by the surgeon results in substantially equal pressures at the multiple blade cutting edges. If properly done, the strip of hair with all hair follicles preserved an be readily removed, divided into individual graft sizes, and replaced in bare scalp areas. The surrounding hair covers the narrow scalped strip.

Problems encountered in implementing the above procedure include: maintaining even cutting pressures on the multiple blades, maintaining the blades parallel, controlling the blade spacings and lengths to match the varying scalp contour and hair follicle arrangement of particular patients to maximize the graft harvest, and avoiding the generation of excessive heat which might damage the hair follicles.

SUMMARY OF THE INVENTION

An object of the invention is medical, dental, or veterinarian cutting instrument construction that reduces the requirements for maintaining even pressures on multiple cutters.

Another object of the invention is an instrument that will enable increased hair follicle grafts in a strip harvesting, hair transplant procedure.

In accordance with one aspect of the invention, the multi-bladed scalpel is replaced by an electrosurgical handpiece with multiple, active, thin electrode wires spaced to perform multiple cuts in human tissue. An immediate advantage is that the electrical currents at the wires tips do the cutting rather than pressured blades; hence, the wire ends can be applied to the tissue with minimum pressure and drawn across the tissue during the incision-making process with virtually no pressure.

Parallel incisions of substantially equal depth are more readily obtained, because (a) only mere contact with virtually no pressure is required for each electrode wire, which is more easily accomplished than if equal pressures had to be applied at multiple edges, and (b) a large improvement in visibility obtains making it easier to cut where desired and to steer around vital hair follicles, i.e., the thin wires present practically no obstacle to the surgeon closely observing the operation, compared with the broader scalpel blades. Moreover, the virtually simultaneous cauterizing of any cut blood vessels minimizes bleeding, which also contributes to improved visibility.

In a preferred embodiment, the electrode wires have different lengths to match the scalp curvature, thus allowing the surgeon desirably to maintain the electrosurgical handpiece substantially perpendicular to the scalp surface.

In accordance with a further aspect of the invention, a multiple-wire electrode construction is provided that allows for varying the lengths of the active wire portions, or varying their spacings, or both. The use of wires, instead of scalpel blades, enables this important feature to be more readily obtained at lower cost. The lower cost allows the electrode part to be disposable. The variable lengths and spacings allows the surgeon to choose wire spacings and lengths that more closely match a particular patients' scalp contour.

A further embodiment of the invention, preferably with the varying spacing construction, provides for insulating of one of the electrodes to be used as a fulcrum about which the other electrode may be rotated when it is desired to make curved incisions.

The various features of novelty which characterize the invention are pointed out with particularity in the claims annexed to and forming a part of this disclosure.

For a better understanding of the invention, its operating advantages and specific objects attained by its use, reference should be had to the accompanying drawings and descriptive matter in which there are illustrated and described the preferred embodiments of the invention.

DETAILED DESCRIPTION OF THE PREFERRED EMBODIMENTS

Figure 1:
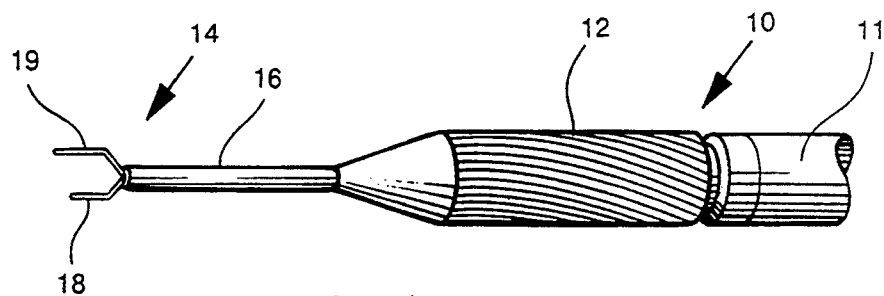
FIG. 1 is a perspective view of a handpiece containing one form of electrosurgical electrode according to the invention.
Figure 5:
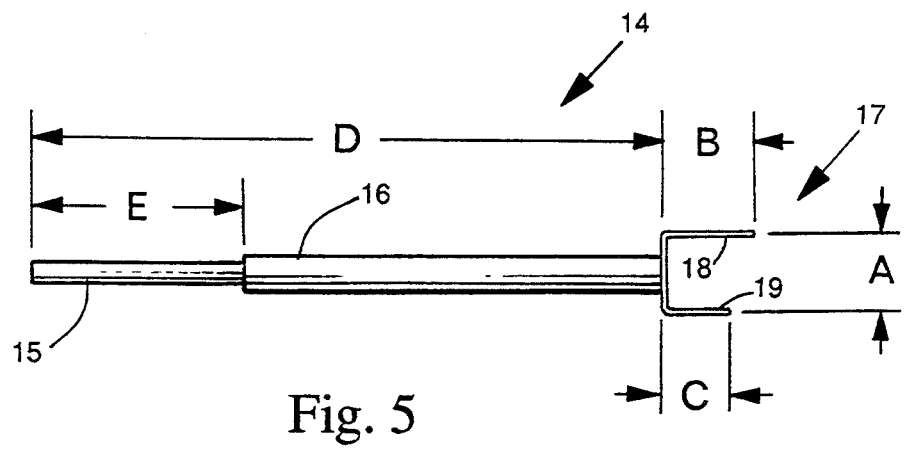
FIGS. 5 and 6 are side views, respectively, of just the electrodes of the FIGS. 1 and 2 embodiments to illustrate sizes and dimensions.

The embodiment of FIG. 1 comprises a conventional electrosurgical handpiece 10 comprising a handle part 11 and an electrode-holding part 12 for receiving and holding an electrode 14 in accordance with one aspect of the invention. The electrode 14 comprises, as also shown in FIG. 5, a shank 15, which is bare at one end (the left end in FIG. 5) and is covered with insulating material 16 over its center part. Connected as by brazing or welding at the opposite shank end is a wire electrode 17 comprising two forwardly-projecting, thin, bare, active wire ends 18, 19, spaced apart by a distance A. As will be observed, one wire end 18 is slightly longer than the other end 19. The lengths are indicated by B and C. For completeness' sake, the overall length of the shank 15 is indicated by D, and the length of the bare end by E. The electrode 14 is typically made of electrically-conductive metal, such as brass. The bare shank end 15 is inserted into the handpiece holding end 12. The latter is typically made as a standard collet construction with a split tube (not shown) on the inside which is sized to receive the shank 15 of the electrode, and with a rotatable nose piece 12 which tightens up on the split tube to tightly hold the tool shank 15 in position. During operation, as is well known, the opposite end of the handpiece 10 is plugged into conventional electrosurgical equipment which generates high-frequency electrical currents which are conveyed via switches (not shown) to the handpiece and through the metal electrode to the active wire ends 18, 19. When the wire ends are applied to animal or human tissue, in a medical, dental, or veterinarian procedure, cutting, coagulation, and various other surgical actions can be caused to take place as a result of the flow of the electrical currents via the wire ends to the tissue.

Figure 7A:
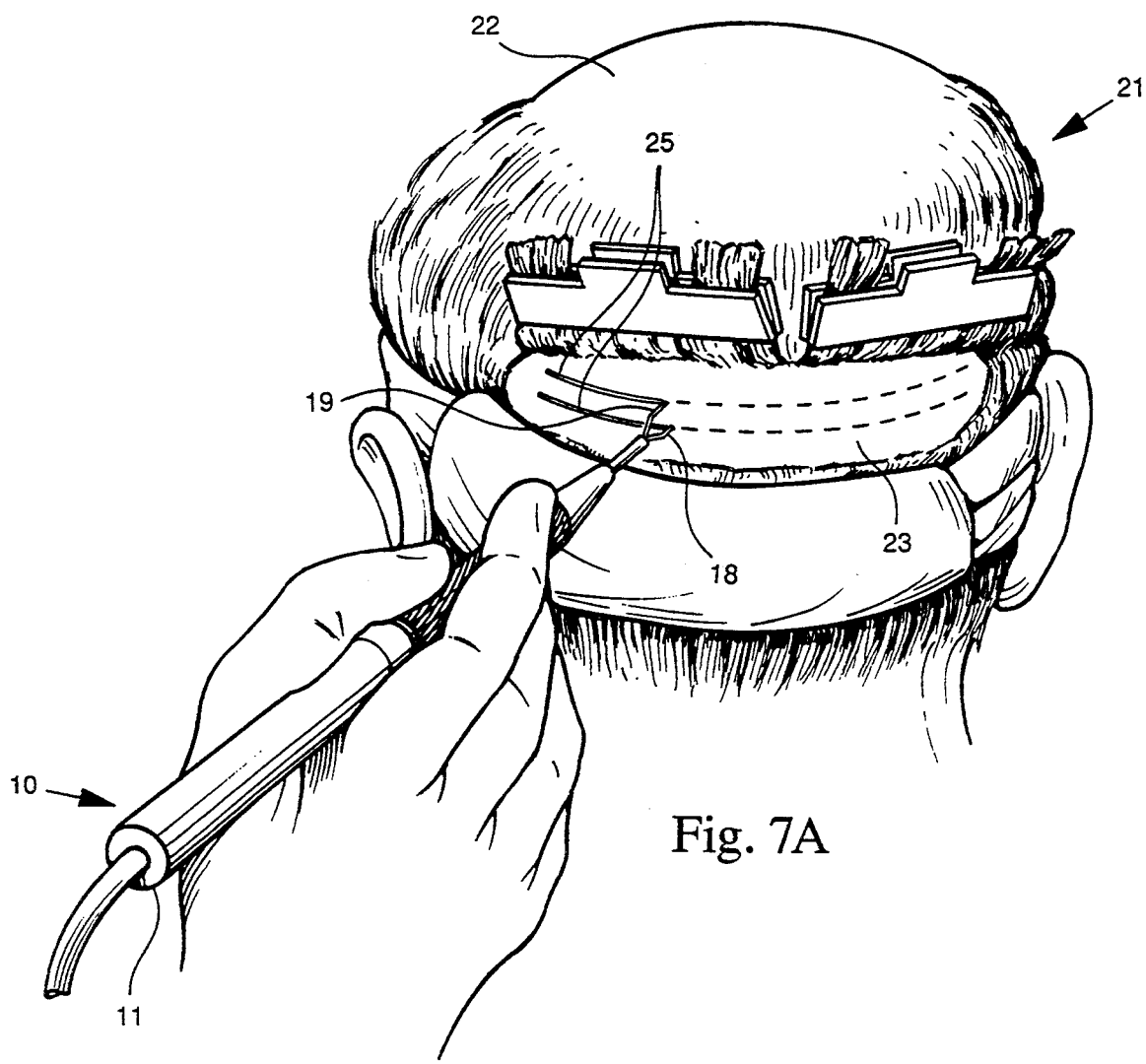
FIGS. 7A and 7B are perspectives view illustrating one way of how the embodiment of FIG. 1 would be used in the course of a hair follicle harvesting procedure.
Figure 7B:
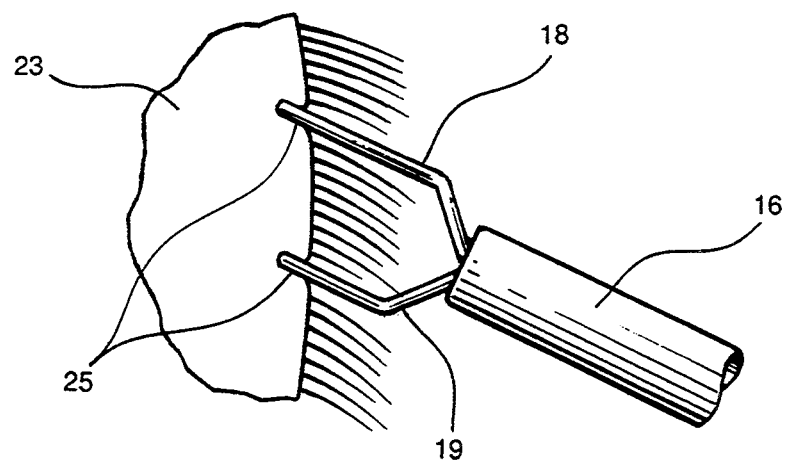

FIG. 7 shows use of the tool of FIG. 1 in a typical graft harvesting operation as part of a hair transplant procedure. The patient's head is designated 21, the hairless scalp area 22 to be implanted with hair, and an area 23 at the rear of the scalp, still covered with hair, from which hair follicles are to be harvested. As noted, the covering hair is peeled back, and the surgeon then makes two parallel incisions 25 in that scalp area 23. Hair is not shown in FIG. 7A for clarity but is shown at 25 in the enlarged view of FIG. 7B. The object is to remove the strip between the incisions, together with the hair follicles, and then replant the hair follicles in the bare scalp area 22. FIG. 7B illustrates the importance of the surgeon having good visibility of the area where the incisions are to be formed in order to avoid damaging any healthy hair follicles to maximize the harvest. The open structure formed by the U-shaped active wire ends 18, 19 provides the good visibility required. Since electrosurgical cutting occurs on mere contact of the exposed electrode wire ends with the tissue, it is much easier for the surgeon to maintain even contact pressure to ensure even cutting depths. The difference in length of the wire ends takes into account the contour of the scalp area and allows the surgeon to position the handpiece to allow him full visibility of the incisions during the procedure.

The spacing of the wire 18, 19 ends is to take into account incision spacings that vary from surgeon to surgeon and from patient to patient. Examples will be given below.

Figure 2:
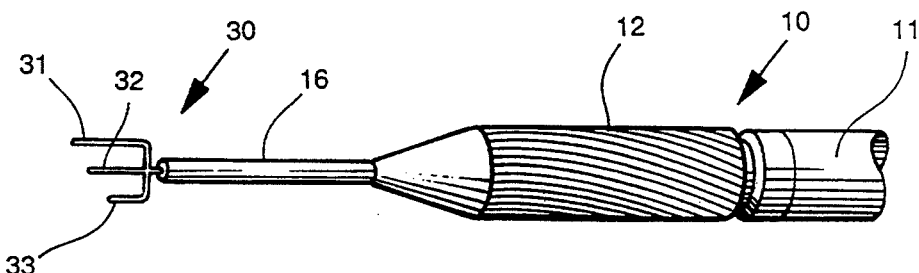
FIG. 2 is a perspective view of a handpiece containing a second form of electrosurgical electrode according to the invention.
Figure 6:
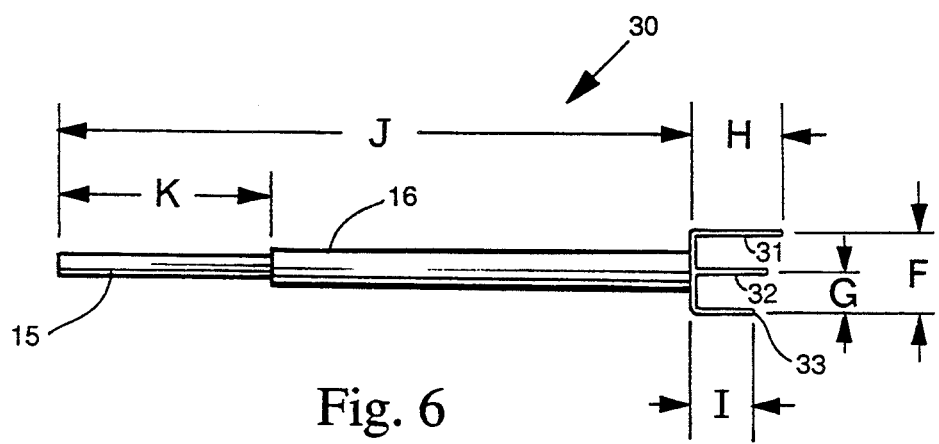

FIG. 2 shows another electrode embodiment 30 according to the invention comprising three wire tines 31, 32, 33 for use by those surgeons who prefer to make three parallel incisions and thereby harvest two strips of tissue with hair follicles. FIG. 6 shows by letters the electrode sizes and dimensions. The Table below lists typical sizes and dimensions for the FIGS. 5 and 6 embodiments, as well as ranges of dimensions suitable for use in hair transplant procedures of the type illustrated in FIG. 6.

TABLE

| DIMENSION | TYPICAL VALUE | RANGE OF VALUES |
| --- | --- | --- |
| A | 4 mm | 4–10 mm |
| B | 0.7 cm | As desired |
| C | 0.5 cm | 50–80% of A |
| D/J | 4.8 cm | As desired |

TABLE-continued

| DIMENSION | TYPICAL VALUE | RANGE OF VALUES |
| --- | --- | --- |
| E/K | 1.6 cm | As desired |
| F | 8 mm | 4–10 mm |
| G | 4 mm | 2–5 mm |
| H | 0.7 cm (center wire 0.6 mm) | As desired |
| I | 0.5 cm | 50–80% of H |

The wire 18,19 diameters can range from 0.004–0.12 inches. The shaft or shank 15 diameters can vary between 1/16 and 3/32 inches. The insulation 16 serves to protect the patient against accidental burns from the electrode. The thin diameters of the wire prongs 18, 19 avoid excessive heat that may damage vital hair follicles.

As mentioned, different surgeons prefer different wire spacings and different wire lengths for certain patients. The FIGS. 3 and 4 embodiment 39 according to the invention provides this capability. The version shown is with three tines or prongs, but is obviously applicable to 2-prong wire electrode configurations or to any number of projecting active wire portions. The construction shown is similar to that used in inexpensive protractors or compasses with some variations. Basically it consists of a center tube 40 similar to a typical known wire or needle electrode onto which are pivoted 41 two additional tubes 43, 44. The latter have an upsetting loop 45 through which are passed in a friction fit the ends of an arc-shaped arm 47 whose ends are capped 48. The arc-shaped member 47 is secured to the center tube 40. It can readily be seen that each of the outer tubes 43, 44 can be pivoted with respect to the center tube 40 to thereby adjust the spacings between the active wire ends. The friction fit maintains the spacings chosen, with little difficulty, especially since virtually no pressure is required to be applied by the wire tips to the patient's tissue.

Figure 4:
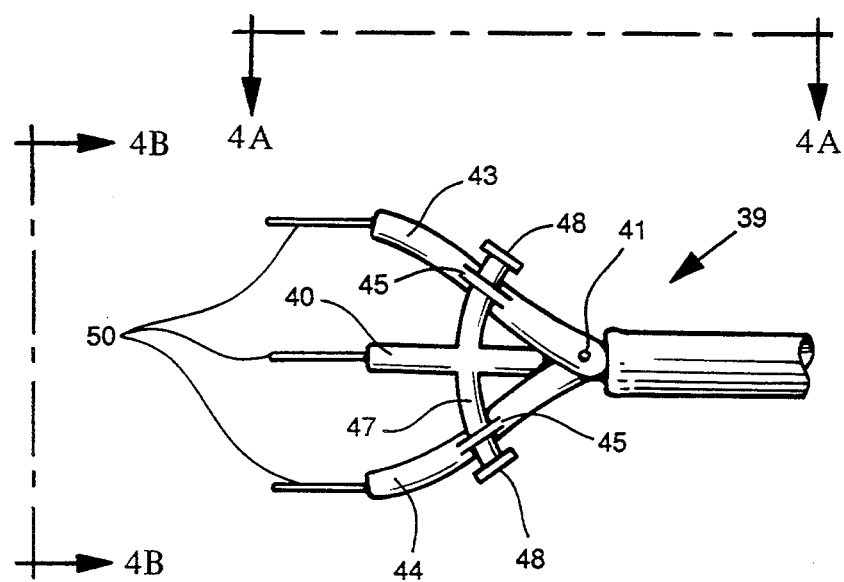
FIG. 4 is an enlarged view of the active electrode end of the electrode of FIG. 3.
Figure 4A:
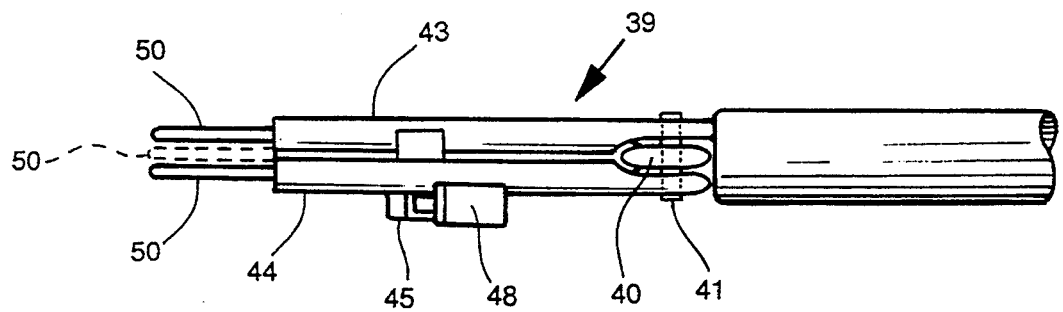
FIGS. 4A and 4B are, respectively, side and end views along the lines 4A and 4B of the electrode of FIG. 4.
Figure 4B:
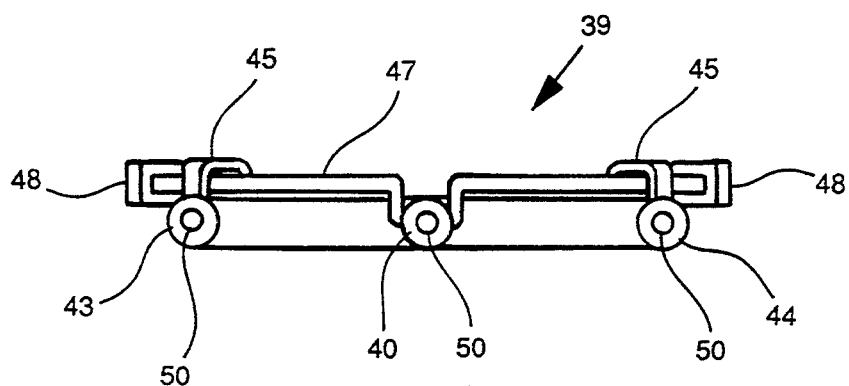

The arm 47, as shown in FIGS. 4A and 4B is configured to attach to the center tube 40 while engaging the loops 45 on top of the two ends tubes 43, 44. The tubes 40, 43, 44 are preferably made of the same bendable brass material typically used by the Ellman Company of Hewlett, N.Y. for its bendable electrodes so that they can be bent to the shape the surgeon desires. Also, the tube ends can be sized and configured so that the wire or needle ends 50 are friction fitted in the tubes, as shown in FIG. 4B, so that they can be moved in and out small distances to allow the surgeon to choose wire lengths that are comfortable. This is similar to the manner in which protractors or compasses hold metal or carbon points. The same principle is also used in the VARI-TIP electrodes sold by the Ellman Company.

It is preferred that the electrosurgical machine or equipment used in the hair transplant procedure is of the type made and sold by the Ellman Company, of Hewlett, N.Y.

Figure 3:
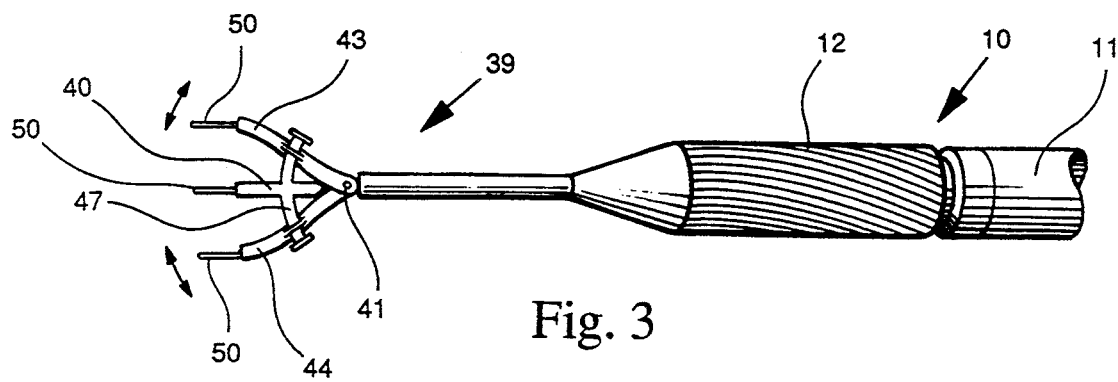
FIG. 3 is a perspective view of a handpiece containing a third form of electrosurgical electrode according to the invention.

It will be evident that the invention is not limited to the construction shown in FIGS. 3 and 4 and other constructions that allow the user or supplier to adjust the active wire spacings and lengths are considered to be within the scope of the invention.

While the invention is best suited for the hair transplant procedure described above, it will be understood that the invention is not limited thereto. There may be other medical, dental, or veterinarian procedures where multiple incisions have to be made, and, to maintain a desired orientation, it would be preferred that the incisions be performed simultaneously with a single instrument. Another possible use is where, for example, a circular incision is desired. In this case, the wire electrodes can be of the same length but with one wire electrode insulated. The instrument would then be used as a compass, with the insulated electrode serving as the center about which the other active wire electrode is rotated to form a circular incision. The same technique would also be usable where arc-shaped incisions are to be made.

While the invention has been described in connection with preferred embodiments, it will be understood that modifications thereof within the principles outlined above will be evident to those skilled in the art and thus the invention is not limited to the preferred embodiments but is intended to encompass such modifications.

What is claimed is:

1. A multiple-wire unipolar electrode for use with an electrosurgical handpiece in an electrosurgical cutting procedure, comprising:
   (a) an electrically-conductive shaft having one end sized to fit on an electrosurgical handpiece and having an end opposite to the one end,
   (b) plural spaced electrically-conductive wires electrically connected to each other and to the opposite end of the shaft and having ends remote from the shaft, the ends of said wires being adjacent and electrically active,
   (d) whereby the wire ends when applied to tissue of a patient and the handpiece energized, electrical currents will flow simultaneously from the wire ends to the tissue allowing simultaneous cutting by electrical currents of parallel incisions when the handpiece is drawn across the tissue.

2. A multiple-wire electrode as claimed in claim 1, wherein one wire end is longer than another wire end.

3. A multiple-wire electrode as claimed in claim 2, wherein the another wire end has a length about 50–80% of that of the longer wire end.

4. A multiple-wire electrode as claimed in claim 1, wherein the electrode comprises only two wire ends.

5. A multiple-wire electrode as claimed in claim 1, wherein the electrode comprises only three spaced wire ends aligned in a single line.

6. A multiple-wire electrode as claimed in claim 1, wherein the wires are spaced apart in the range of 2–10 mm.

7. A multiple-wire electrode as claimed in claim 1, wherein the wire ends have diameters in the range of 0.004–0.12 inches.

8. A multiple-wire electrode for use with an electrosurgical handpiece in an electrosurgical procedure, comprising:
   (a) an electrically-conductive shaft having one end sized to fit on an electrosurgical handpiece and having an end opposite to the one end,
   (b) plural spaced electrically-conductive wires extending from the opposite end of the shaft and electrically connected to the opposite end of the shaft and having ends remote from the opposite end of the shaft, the ends of said wires being electrically active, whereby the wire ends when applied to tissue of a patient and the handpiece energized, electrical currents will flow simultaneously from the wire ends to the tissue allowing simultaneous cutting by electrical currents of parallel incisions when the handpiece is drawn across the tissue,
   (c) means connected to the shaft for varying the spacing between the wire ends.

9. A multiple-wire electrode as claimed in claim 8, further comprising means for adjusting the lengths of the wire ends.

10. A multiple-wire electrode for use with an electrosurgical handpiece in an electrosurgical procedure, comprising:
    (a) an electrically-conductive shaft having one end sized to fit on an electrosurgical handpiece and having an end opposite to the one end,
    (b) plural spaced electrically-conductive wires electrically connected to the opposite end of the shaft and having ends remote from the shaft, the end of at least one of said wires remote from the shaft being electrically active,
    (c) means for varying the spacing between the wire ends,
    (d) whereby the active wire end when applied to tissue of a patient and the handpiece energized, electrical currents will flow from the active wire end to the tissue allowing cutting by electrical currents of an incision relative to the end of another one of said wires when the handpiece is drawn across the tissue.

11. A multiple-wire unipolar electrode in combination with an electrosurgical handpiece for use in an electrosurgical cutting procedure, comprising:
    (a) an electrosurgical handpiece having an elongated handle and at one end an opening sized to receive a shaft of a unipolar electrode,
    (b) an electrically-conductive shaft having one end fitted within the opening at said one end of the electrosurgical handpiece and having an opposite end, said shaft extending in the same direction as the elongated handle,
    (c) plural spaced electrically-conductive wires electrically connected to each other and to the opposite end of the shaft and having ends remote from the shaft, the ends remote from the shaft of at least two of said wires being adjacent and electrically active,
    (d) whereby the active wire ends when applied to tissue of a patient and the handpiece energized, electrical currents will flow from the active wire ends to the tissue allowing cutting by electrical currents of spaced incisions corresponding to the wire end spacing when the handpiece is drawn by its handle across the tissue.

12. A multiple-wire electrode as claimed in claim 11, wherein, measured form the opposite end of the shaft, one of the wires is shorter than another one of the wires adjacent to the one wire.

* * * * *